United States Patent [19]

Sato et al.

[11] Patent Number: 5,663,403

[45] Date of Patent: Sep. 2, 1997

[54] BISPHOSPHITE COMPOUND AND METHOD FOR PRODUCING ALDEHYDES

[75] Inventors: Keiichi Sato; Eitaro Takahashi; Yoshifumi Tanihara; Yasuhiro Wada, all of Yokohama, Japan

[73] Assignee: Mitsubishi Chemical Corporation, Tokyo, Japan

[21] Appl. No.: 588,390

[22] Filed: Jan. 18, 1996

[30] Foreign Application Priority Data

Jan. 24, 1995 [JP] Japan .................................. 7-008924

[51] Int. Cl.$^6$ ...................................... C07F 9/06
[52] U.S. Cl. ........................................... 558/156
[58] Field of Search ............................. 558/156; 568/14, 568/17

*Primary Examiner*—C. Warren Ivy
*Assistant Examiner*—Jean F. Vollano
*Attorney, Agent, or Firm*—Oblon, Spivak, McClelland, Maier & Neustadt, P.C.

[57] ABSTRACT

A bisphosphite compound of the following formula (I):

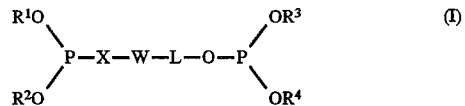

wherein W is a substituted or unsubstituted arylene group, L is a substituted or unsubstituted alkylene or alkenylene group, X is an oxygen atom, and each of $R^1$ to $R^4$ which are the same or different, is a substituted or unsubstituted alkyl, aryl, alkylaryl, arylalkyl or alicyclic group, or $R^1$ and $R^2$, and/or $R^3$ and $R^4$, bond to each other to form a ring.

12 Claims, No Drawings

BISPHOSPHITE COMPOUND AND METHOD FOR PRODUCING ALDEHYDES

BACKGROUND OF THE INVENTION

1. Field of the Invention

The present invention relates to a novel bisphosphite compound and a method for producing aldehydes by subjecting an olefinic compound to a hydroformylation reaction in the presence of a catalyst containing such a phosphite compound and a Group VIII metal.

2. Discussion of Background

The reaction which comprises reacting an olefinic compound with carbon monoxide and hydrogen in the presence of a catalyst in a solvent to produce aldehydes or alcohols as their hydrogenated products, is well-known as hydroformylation reaction. As the catalyst, it is common to use a soluble complex of a Group VIII metal having an organic phosphorus compound as a ligand. The ligand used together with the metal component of the catalyst gives substantial influence to the catalytic reaction. Also in the hydroformylation reaction, it is widely known that the catalytic activity and the selectively are substantially influenced by the ligand. In order to carry out the hydroformylation reaction industrially advantageously, it is important to improve the catalytic activity and the selectivity of the product. Accordingly, various efforts to design the ligand have been made for this purpose.

Various phosphite compounds are known as a group of phosphorus compounds which may be used as the ligands. In addition to monophosphites such as trialkylphosphites or triarylphosphites, various phosphite compounds including polyphosphites having plural coordinating phosphorus atoms in their molecules, have been proposed. For example, Japanese Unexamined Patent Publications No. 116587/1987 and No. 116535/1987 disclose bisphosphite compounds containing two phosphorus atoms in their molecules. Further, Japanese Unexamined Patent Publication No. 178779/1993 discloses bisphosphite compounds having a β-naphthyl group or a phenyl group substituted at a specific position.

As mentioned above, various phosphite compounds have been proposed as the ligand to be used for the hydroformylation reaction. However, the selectivity of the desired product formed in the hydroformylation reaction using these compounds have not necessarily been satisfied, and the formation of by-products has brought about an economical disadvantage to commercial production. Among such by-products, paraffins formed by reduction of an olefinic compound with hydrogen without a hydroformylation reaction, are particularly valueless, since they are not useful other than as fuels. Accordingly, it has been desired to develop a phosphite ligand which does not cause such a reduction reaction as a side-reaction.

SUMMARY OF THE INVENTION

In the course of a search for an effective ligand to improve and maintain the catalytic activity and the selectivity of the desired product in the hydroformylation reaction, the present inventors have found a novel nonsymmetric bisphosphite compound having a certain specific structure and have further found that when such a compound is used as a ligand, good results can be obtained with respect to the catalytic activity for the hydroformylation reaction and the selectivity of a straight chain isomer as an aldehyde product, and at the same time, the reduction reaction as a side-reaction can be suppressed. The present invention has been accomplished on the basis of these discoveries.

That is, in a first aspect, the present invention provides a bisphosphite compound having the following formula (I):

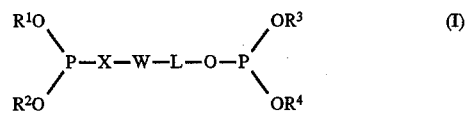

wherein W is a substituted or unsubstituted arylene group, L is a substituted or unsubstituted alkylene or alkenylene group, X is an oxygen atom, and each of $R^1$ to $R^4$ which are the same or different, is a substituted or unsubstituted alkyl, aryl, alkylaryl, arylalkyl or alicyclic group, or $R^1$ and $R^2$, and/or $R^3$ and $R^4$, bond to each other to form a ring.

Further, in a second aspect, the present invention provides a method for producing aldehydes, which comprises reacting an olefinic compound with carbon monoxide and hydrogen in the presence of a catalyst containing a Group VIII metal and a phosphite compound to obtain the corresponding aldehydes, wherein a bisphosphite compound having the following formula (I) is used as the phosphite compound:

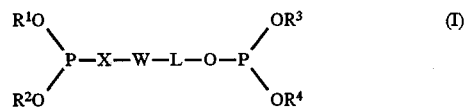

wherein W is a substituted or unsubstituted arylene group, L is a substituted or unsubstituted alkylene or alkenylene group, X is an oxygen atom, and each of $R^1$ to $R^4$ which are the same or different, is a substituted or unsubstituted alkyl, aryl, alkylaryl, arylalkyl or alicyclic group, or $R^1$ and $R^2$, and/or $R^3$ and $R^4$, bond to each other to form a ring.

DETAILED DESCRIPTION OF THE PREFERRED EMBODIMENTS

Now, the present invention will be described in detail.

The phosphite compound of the present invention is a novel bisphosphite compound having the following formula (I):

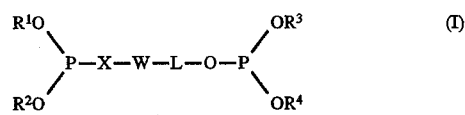

In the formula (I), the organic group represented by W is a substituted or unsubstituted arylene group such as a substituted or unsubstituted phenylene, naphthylene, anthracenylene group. Among them, substituted or unsubstituted 1,2-phenylene, 1,2-naphthylene and 2,3-naphthylene group are preferred. The substituent of W may, for example, be a straight chain or branched chain alkyl group having from 1 to 12, preferably from 1 to 8, carbon atoms, such as methyl, ethyl, propyl, butyl or pentyl, an alkoxy group having from 1 to 12, preferably from 1 to 8, carbon atoms, such as methoxy or ethoxy, or an aryl group having from 6 to 22, preferably from 6 to 14, carbon atoms such as phenyl. From one to three such substituents may be substituted on the aromatic ring of the arylene group. Specifically, W includes, for example, a 1,2-phenylene group, a 1,3-phenylene group, a 4-t-butyl-1,2-phenylene group, a 4-methoxy-1,2-phenylene group, a 3,5-dimethyl-1,2-phenylene group, a 1,2-naphthylene group, a 1,3-naphthylene group, a 2,3-naphthylene group, a 1,8-naphthylene group, a 3-t-butyl-1,2-naphthylene group, a 3,6-di-t-butyl-1,2-naphthylene group, a 1,2-anthracenylene group, a 2,3-anthracenylene group and a 1-(1-naphthyl)-2,3-naphthylene group. Among them, a 1,2-pheneyelne group, a 4-t-butyl-1,2-phenylene group and a 3,5-dimethyl-1,2-phenylene group are preferred.

The organic group represented by L is a substituted or unsubstituted alkylene or alkenylene group, which preferably has from 1 to 6 carbon atoms. The substituent for L may, for example, be a straight chain or branched alkyl group having from 1 to 12, preferably from 1 to 8, carbon atoms such as methyl, ethyl, propyl, butyl or pentyl, an alkoxy group having from 1 to 12, preferably from 1 to 8, carbon atoms such as methoxy or ethoxy, an aryl group having from 6 to 22, preferably from 6 to 14, carbon atoms such as phenyl. Specifically, L includes, for example, a methylene group, a 1,2-ethylene group, a methylmethylene group, a phenylmethylene group, a 1,3-propylene group, an isopropylmethylene group, a cis-vinylene group and a trans-vinylene group.

In the above formula (I), X is an oxygen atom. The crosslinking structure —W—L— for the two phosphite moieties may be any optional combination of the above described W and L. However, it is preferred that the X-atom and the O-atom are apart from each other by from 4 to 10 covalent bonds through W and L. Here, the concept of covalent bond should be understood to include such aromatic bonds as a carbon-carbon bond between neighboring two carbon atoms in benzene ring. In a more preferred structure, W is an arylene group wherein two carbon atoms on an aromatic ring bonding to X and L are adjacent to each other. Specifically, it is a structure corresponding to 2-hydroxymethylphenol, 2-hydroxymethyl-5-t-butylphenol, 2-hydroxymethyl-4,6-dimethyl phenol, 2-(2-hydroxyethyl) phenol or 2-(2-hydroxyethyl)-4,6-dimethylphenol.

Each of $R^1$, $R^2$, $R^3$ and $R^4$ which are the same or different, is a substituted or unsubstituted alkyl, aryl, alkylaryl, arylalkyl or alicyclic group, or $R^1$ and $R^2$, and/or $R^3$ and $R^4$ bond to each other to form a ring. Each of $R^1$ to $R^4$ is preferably a group having the following formula (II):

In the formula (II), the organic group represented by $Q^1$ is a substituted or unsubstituted aryl group such as phenyl, naphthyl or anthracenyl, a substituted or unsubstituted arylene group such as phenylene, naphthylene or anthracenylene, or a substituted or unsubstituted cycloalkyl group such as cyclohexyl or cyclooctyl, and $Q^1$ in each of $R^1$ and $R^3$ in the formula (I) may form a covalent bond directly, or via a substituent on $Q^1$, with the phosphite oxygen atom adjacent to $R^2$ or $R^4$ in the formula (I). The substituent for $Q^1$ may, for example, be a straight chain or branched chain alkyl group having from 1 to 12, preferably from 1 to 8, carbon atoms, such as methyl, ethyl, propyl, butyl or pentyl, an alkoxy group having from 1 to 12, preferably from 1 to 8, carbon atoms such as methoxy or ethoxy, or an aryl group having from 6 to 22, preferably from 6 to 14, carbon atoms such as phenyl. From 1 to 3 such substituents may be substituted on the aromatic ring of the arylene group.

The organic group represented by $R^5$ is a substituted or unsubstituted alkyl or alkenyl group having from 1 to 6 carbon atoms, or a substituted or unsubstituted alkylene or alkenylene group having from 1 to 6 carbon atoms. $R^5$ in each of $R^1$ and $R^3$ in the formula (I) may form a covalent bond directly, or via a substituent on $R^5$, with the phosphite oxygen atom adjacent to $R^2$ or $R^4$ in the formula (I). The substituent for $R^5$ may, for example, be a straight chain or branched chain alkyl group having from 1 to 12, preferably from 1 to 8, carbon atoms such as methyl, ethyl, propyl, butyl or pentyl, an alkoxy group having from 1 to 12, preferably from 1 to 8, carbon atoms such as methoxy or ethoxy, or an aryl group having from 6 to 22, preferably from 6 to 14, carbon atoms such as phenyl. From 1 to 3 such substituents may be substituted on the aromatic ring of the arylene group.

In the formula (II), each of m and n is an integer of 0 or 1, and at least one of them is 1. However, when $R^1$ and $R^2$, or $R^3$ and $R^4$, bond to each other, m and n in $R^2$ or $R^4$ may be 0 at the same time. In such a case, $R^1$ or $R^3$ is connected to the phosphite oxygen atom directly or via a substituent.

A preferred structure for each of $R^1$ to $R^4$ is a substituted or unsubstituted aryl group. Specifically, it is a substituted or unsubstituted aryl group such as substituted or unsubstituted phenyl, naphthyl or anthracenyl. The substituent for each of $R^1$ to $R^4$ may, for example, be a straight chain or branched chain alkyl group having from 1 to 12, preferably from 1 to 8, carbon atoms, such as methyl, ethyl, propyl, butyl or pentyl, an alkoxy group having from 1 to 12, preferably from 1 to 8, carbon atoms, such as methoxy or ethoxy, an aryl group having from 6 to 22, preferably from 6 to 14, carbon atoms, such as phenyl. From 1 to 3 such substituents may be substituted on the aromatic ring of the aryl group.

Another preferred structure for $R^1$ to $R^4$ is a structure wherein $R^1$ and $R^2$, and/or $R^3$ and $R^4$, together form a single arylene group which may have a substituent such as 1,2-phenylene, or a structure having two arylene groups linked as represented by the following formula (III):

In the formula (III), the organic group represented by each of $Q^2$ and $Q^3$ is a substituted or unsubstituted arylene group such as substituted or unsubstituted phenylene, naphthylene or anthracenylene. $Q^2$ and $Q^3$ may be the same or different. The substituent for each of $Q^2$ and $Q^3$ may, for example, be a straight chain or branched alkyl group having from 1 to 12, preferably from 1 to 8, carbon atoms such as methyl, ethyl, propyl, butyl or pentyl, an alkoxy group having from 1 to 12, preferably from 1 to 8, carbon atoms such as methoxy or ethoxy, and an aryl group having from 6 to 22, preferably from 6 to 14, carbon atoms such as phenyl. From 1 to 3 such substituents may be substituted on each aromatic ring of the two arylene groups.

The structure represented by $R^6$ is a bivalent crosslinking group such as a substituted or unsubstituted alkylene group such as methylene, hydroxymethylene or hydroxyphenylmethylene, a ketone-form CO group, an ether-form oxygen atom, a substituted or unsubstituted amino group such as NH, NMe or NPh, a thioether-form sulfur atom, a sulfoxide-form SO group, or a sulfone-form $SO_2$ group. (Me represents a methyl group, and Ph represents a phenyl group.)

In the formula (III), p is an integer of 0 or 1, and p=0 means that $Q^2$ and $Q^3$ are linked directly by a covalent bond.

A more preferred structure for each of $R^1$ to $R^4$ is a phenyl group having a hydrocarbon group at least at the o-position or a β-naphthyl group having a hydrocarbon group at least at the 3-position.

Here, the phenyl group having a hydrocarbon group at the o-position may, for example, be 2-t-butylphenyl, 2,4-di-t-butylphenyl, 2-isopropylphenyl, 2-t-amylphenyl, 2,4-di-t-amylphenyl, 2-s-butylphenyl, 6-t-butyl-2,4-xylyl, 2-t-butyl- 4-methoxyphenyl, 2-t-butyl-4-phenylphenyl, 2-t-butyl-4-tolyl, 2-t-butyl-4-(methoxycarbonyl)phenyl or 2-phenylphenyl.

Likewise, the β-naphthyl group having a hydrocarbon group at the 3-position may, for example, be 3-t-butyl-2-naphthyl, 3,6-di-t-butyl-2-naphthyl, 3,6,8-tri-t-butyl-2-naphthyl, 3-isopropyl-2-naphthyl, 3,6-diisopropyl-2-naphthyl, 3,6,8-triisopropyl-2-naphthyl, 3-t-amyl-2-naphthyl, 3,6-di-t-amyl-2-naphthyl or 3,6,8-tri-t-amyl-2-naphthyl.

Another more preferred structure for $R^1$ to $R^4$ may be a structure wherein $R^1$ and $R^2$, and/or $R^3$ and $R^4$, together form a single arylene group which may have a substituent such as 1,2-phenylene, or a structure having two arylene groups linked as represented by the following formula (IV):

   (IV)

In the formula (IV), the organic group represented by each of $Q^5$ and $Q^6$ is a substituted or unsubstituted arylene group, and $Q^5$ and $Q^6$ bond to each other at their o-positions by a covalent bond. $Q^5$ and $Q^6$ may be the same or different. The substituent for each of $Q^5$ and $Q^6$ may, for example, be a straight chain or branched alkyl group having from 1 to 12, preferably from 1 to 8, carbon atoms such as methyl, ethyl, propyl, butyl or pentyl, an alkoxy group having from 1 to 12, preferably from 1 to 8, carbon atoms such as methoxy or ethoxy, and an aryl group having from 6 to 22, preferably from 6 to 14, carbon atoms such as phenyl. From 1 to 3 such substituents may be substituted on each aromatic ring of the two arylene groups.

The single arylene group which may have a substituent may, for example, be 1,2-phenylene, and the group of the formula (IV) may, for example, be a 2,2'-biphenylene group, a 3,3',5,5'-tetra-t-butyl-2,2'-biphenylene group or a 3,3'-di-t-butyl-5,5'-dimethoxy-2,2'-biphenylene group, as a preferred structure.

Typical examples of the bisphosphite compound of the formula (I) of the present invention will be given below.

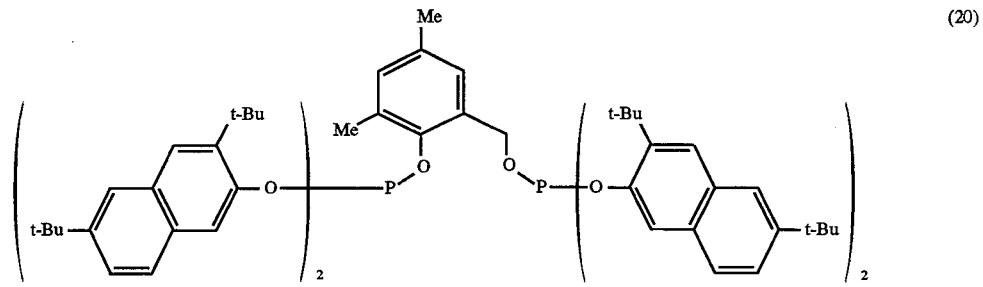

(20)

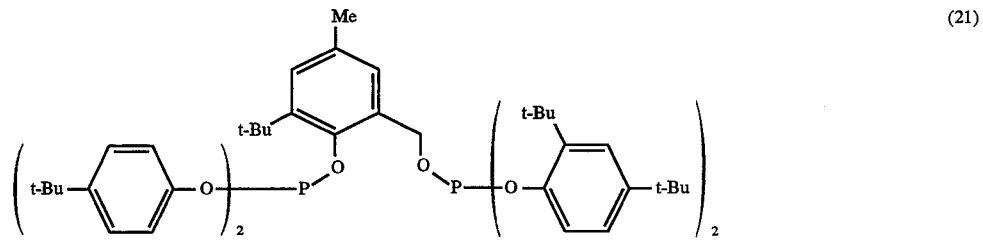

(21)

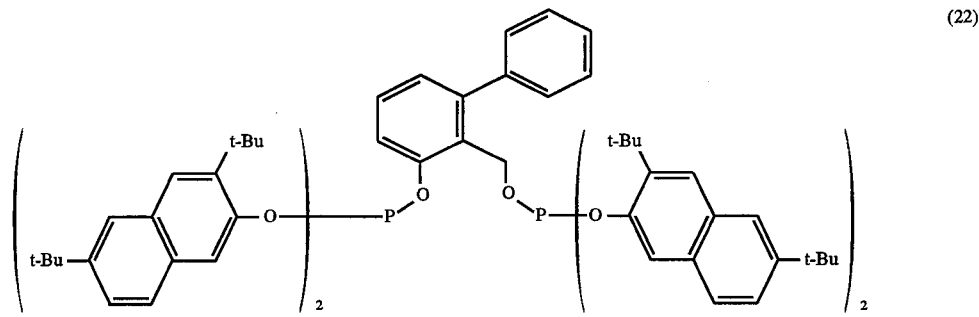

(22)

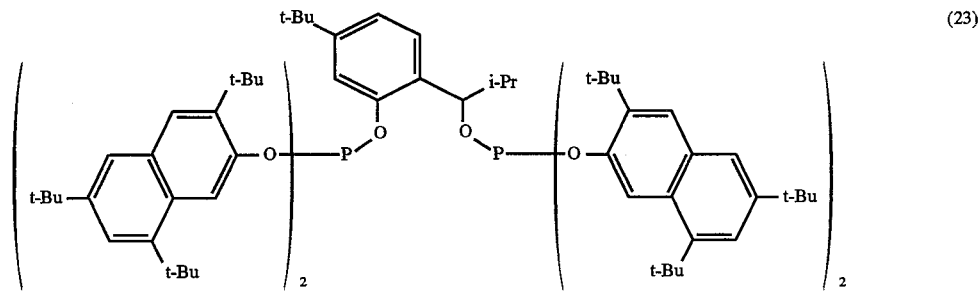

(23)

-continued
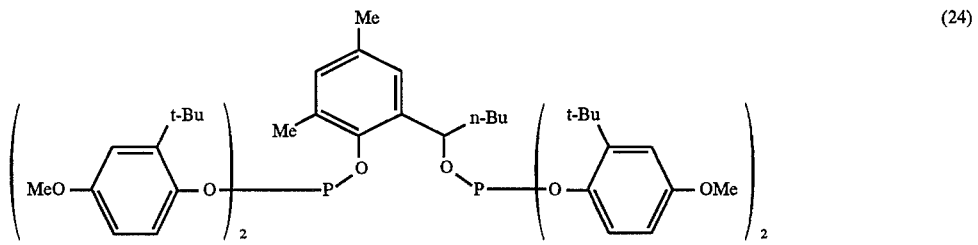
(24)
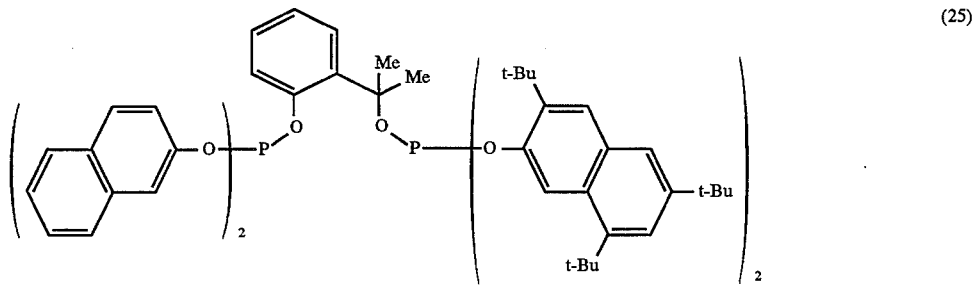
(25)
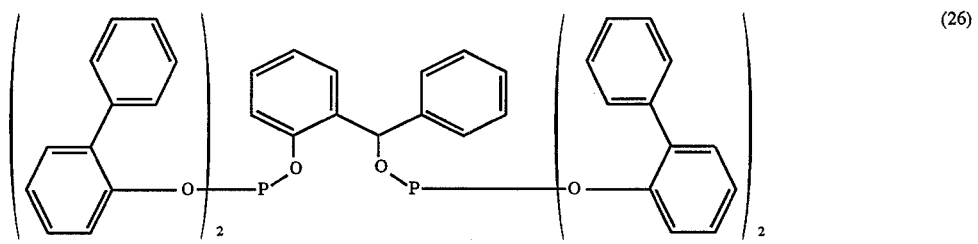
(26)
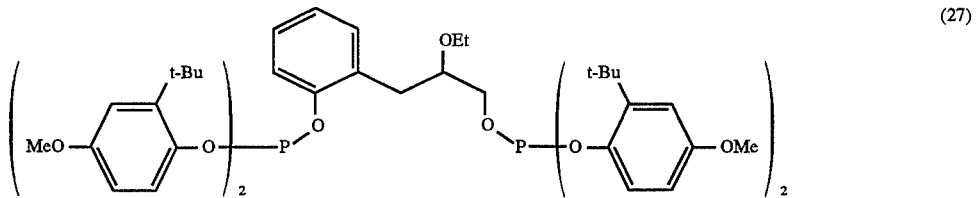
(27)
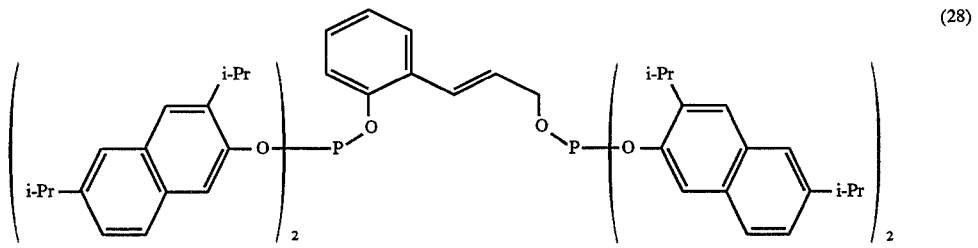
(28)
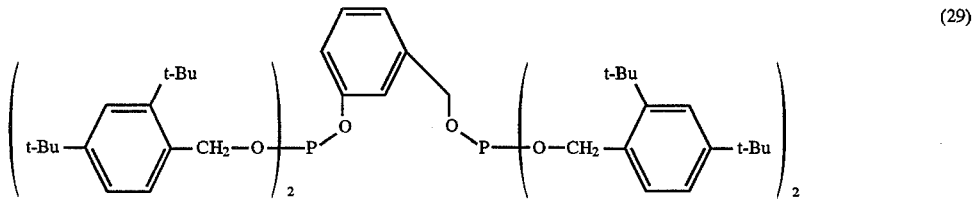
(29)
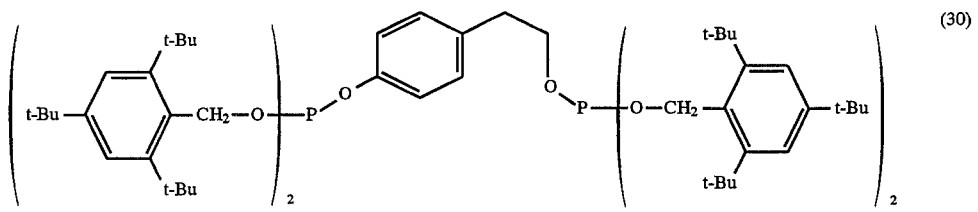
(30)

-continued
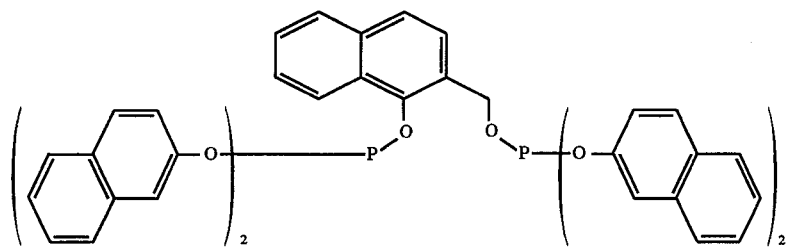
(31)
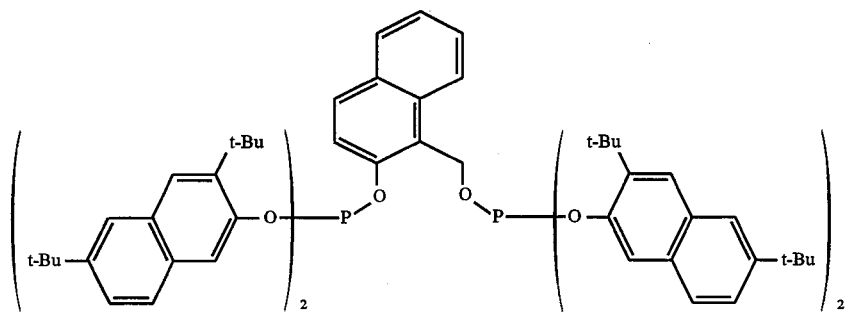
(32)
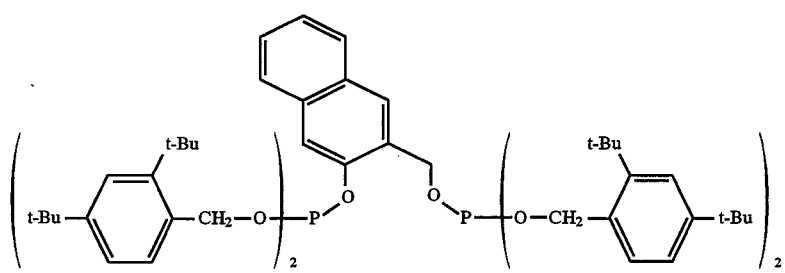
(33)
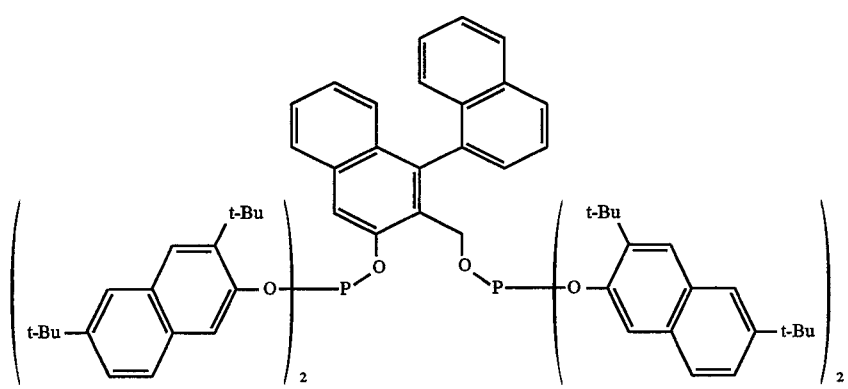
(34)
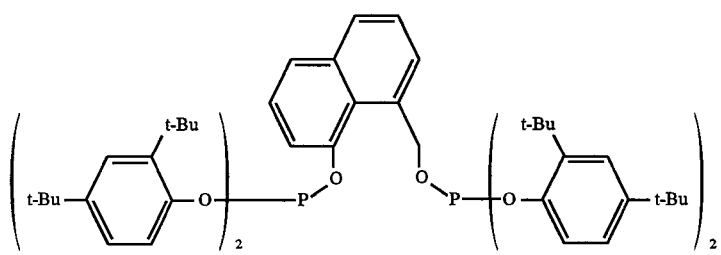
(35)

-continued
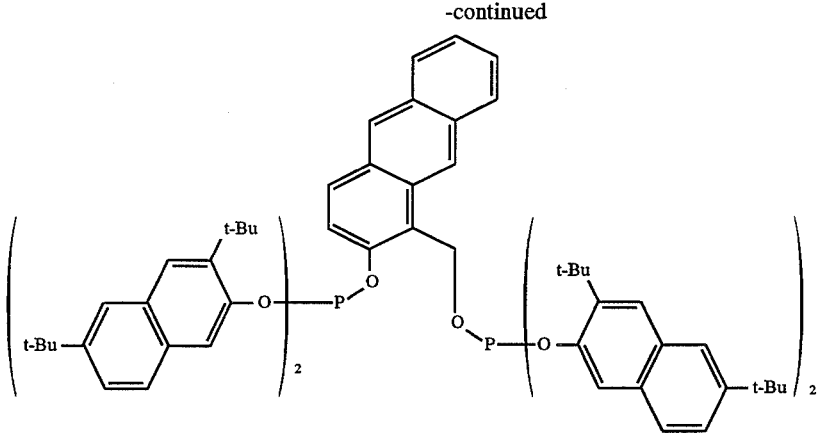
(36)
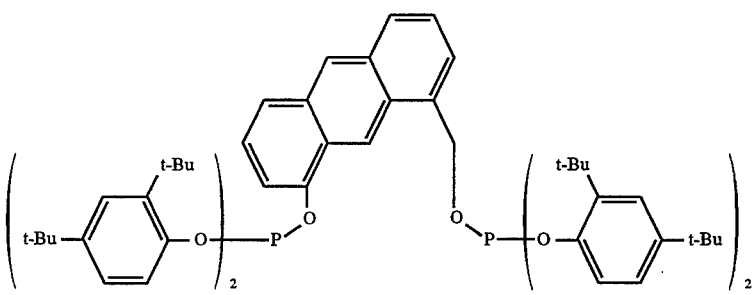
(37)
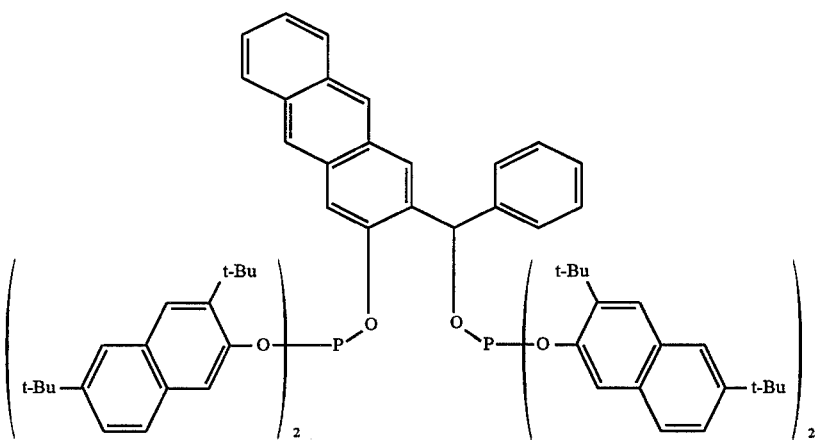
(38)
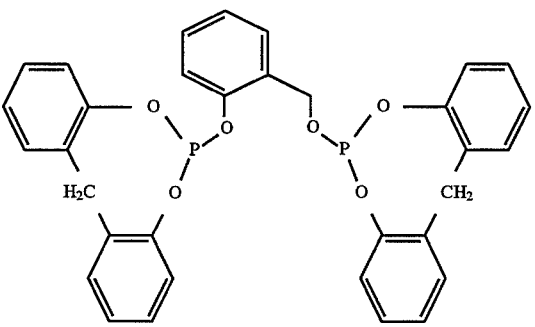
(39)

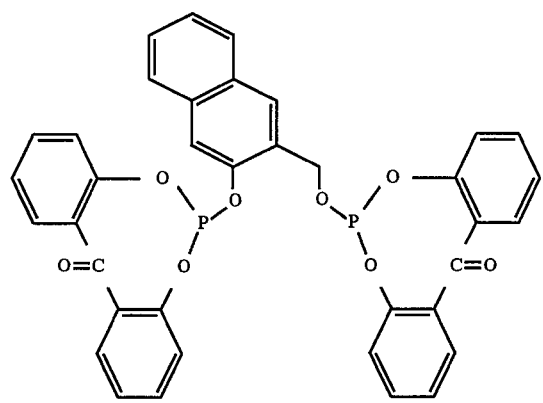
(40)
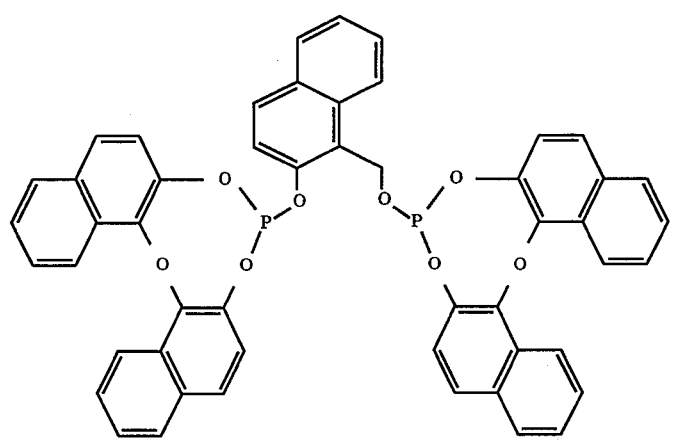
(41)
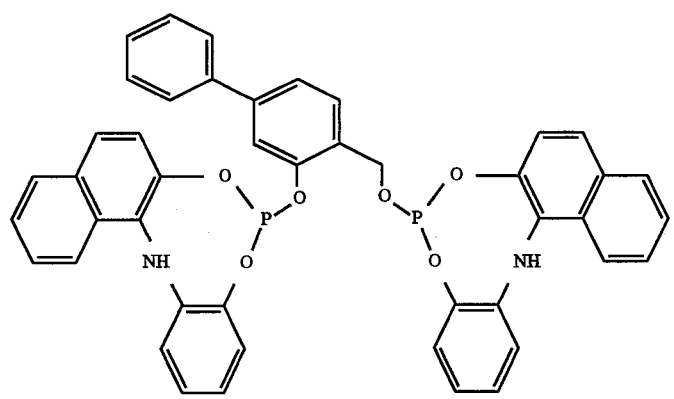
(42)
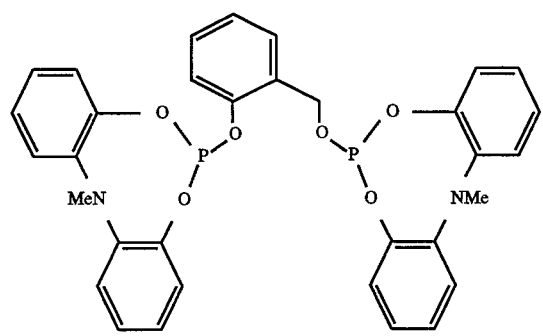
(43)

(44)
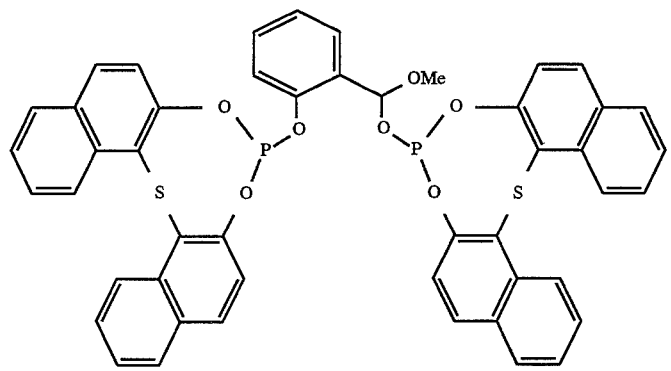
(45)
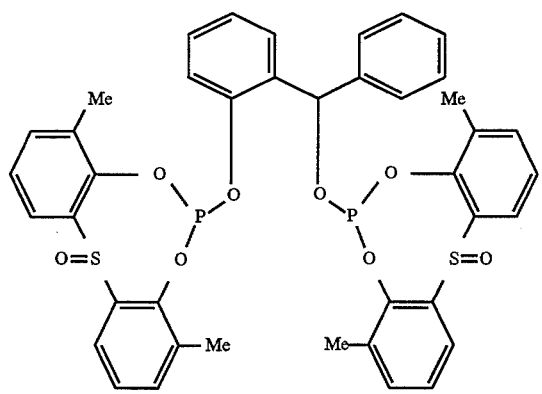
(46)
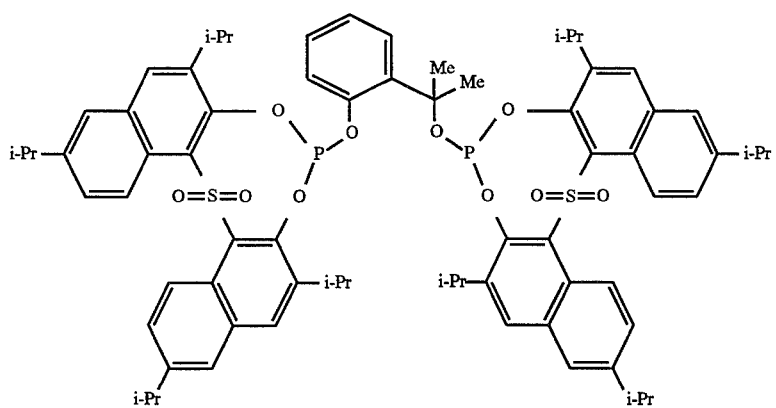
(47)
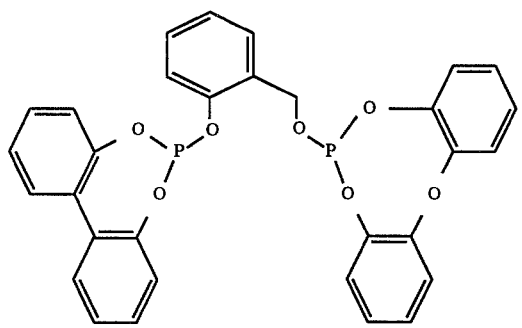

-continued
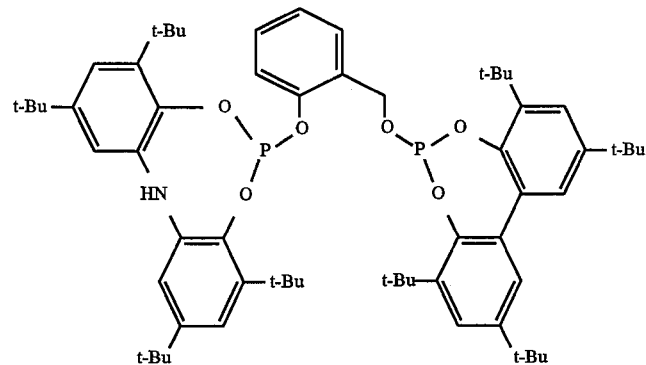
(48)
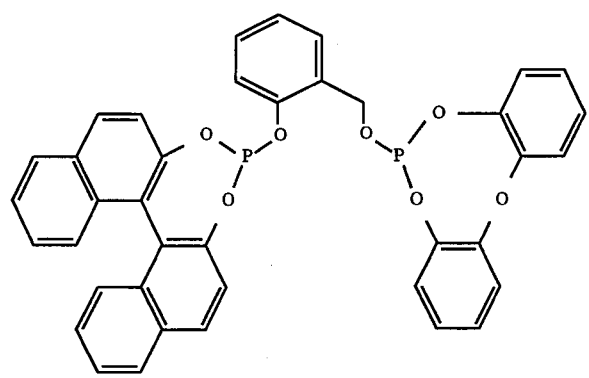
(49)
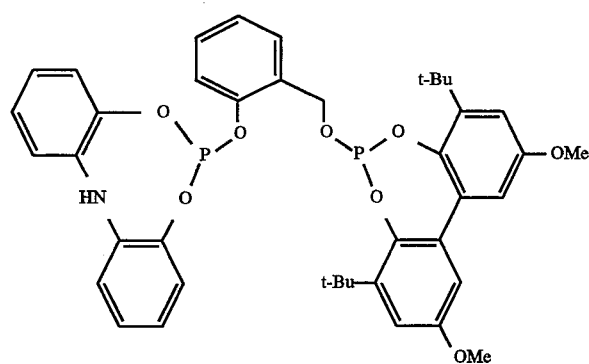
(50)
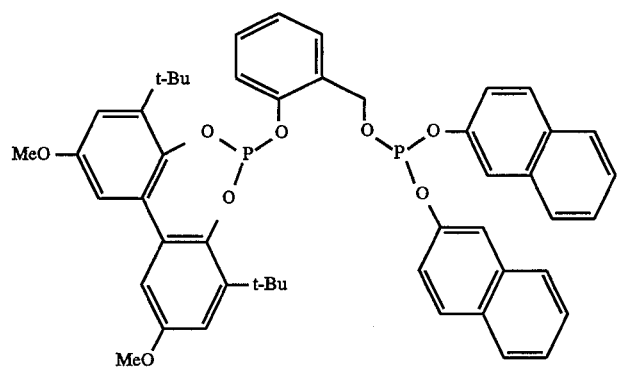
(51)

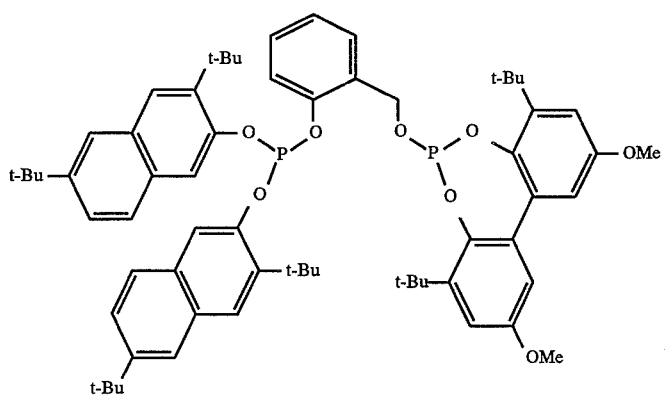
(52)
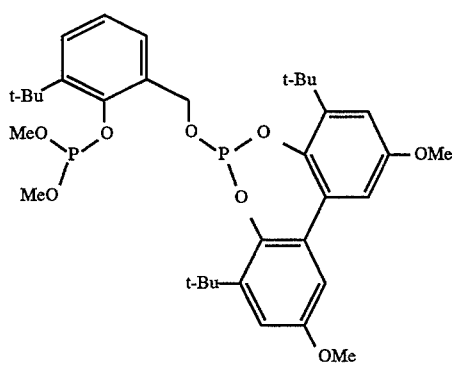
(53)
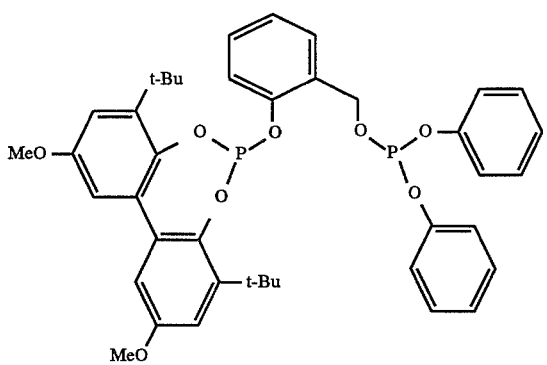
(54)
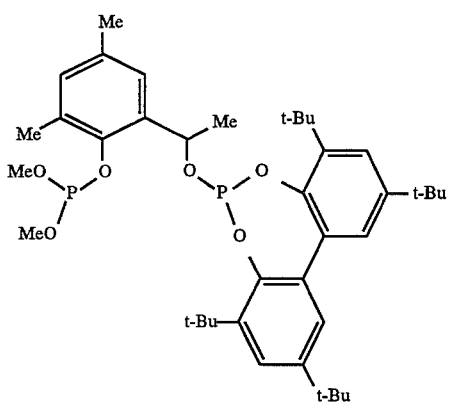
(55)

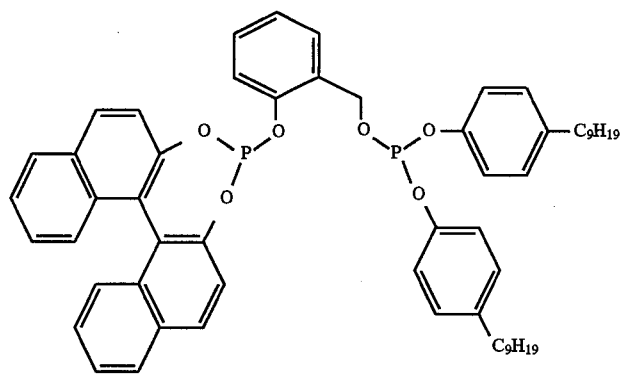
(56)
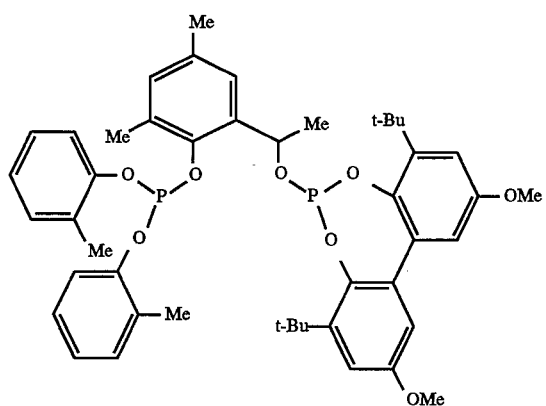
(57)
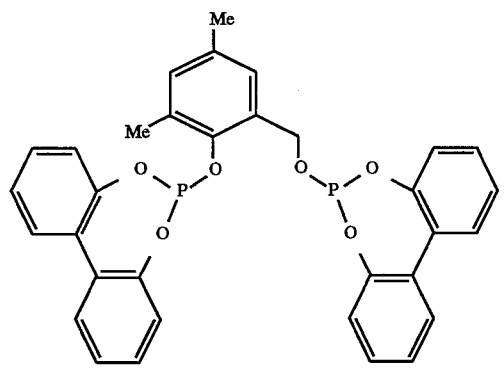
(58)
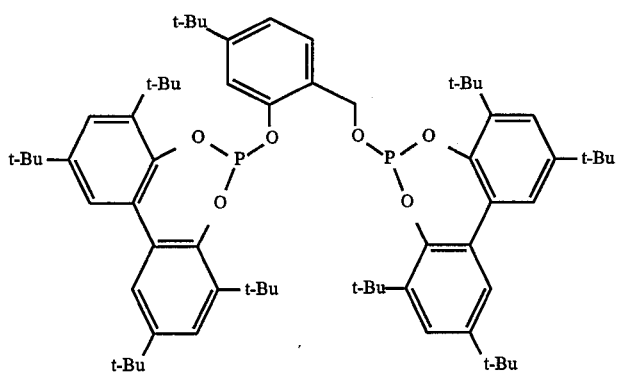
(59)

-continued
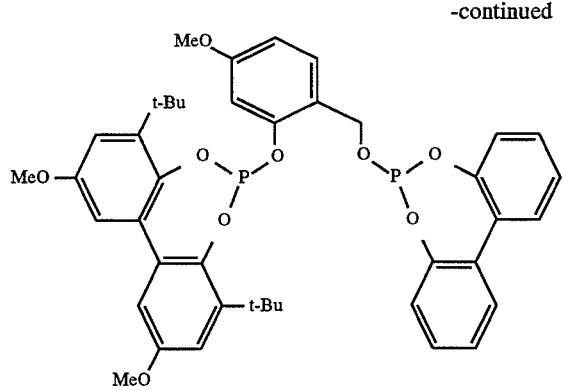
(60)
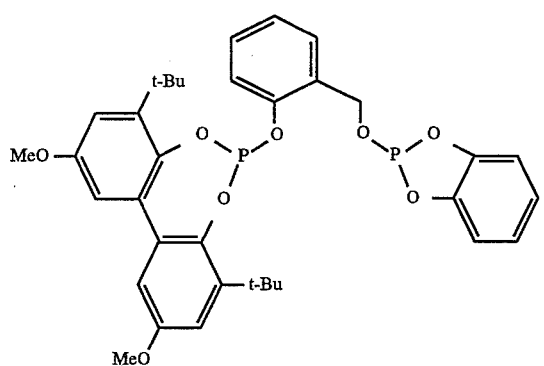
(61)
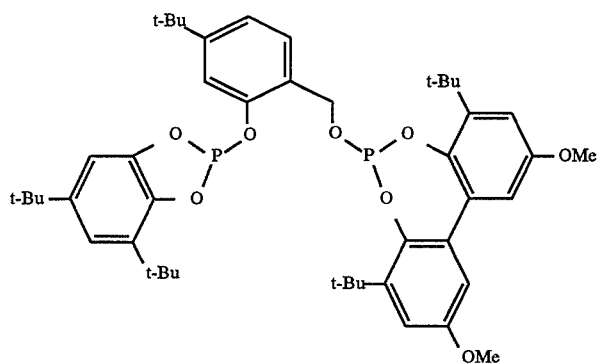
(62)
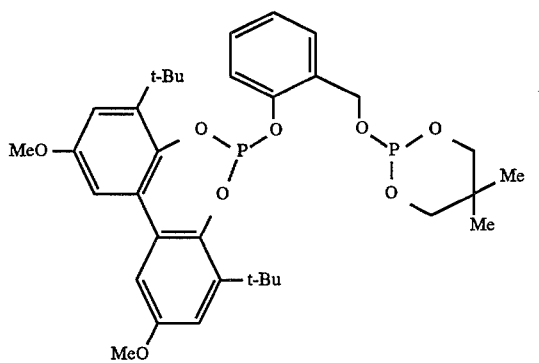
(63)

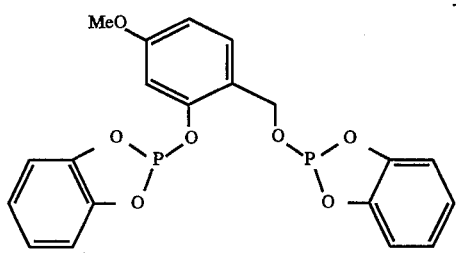

(64)

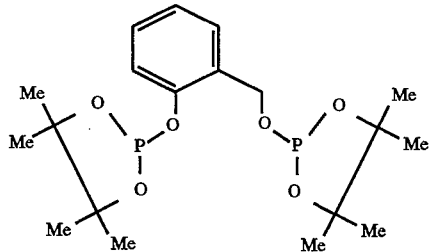

(65)

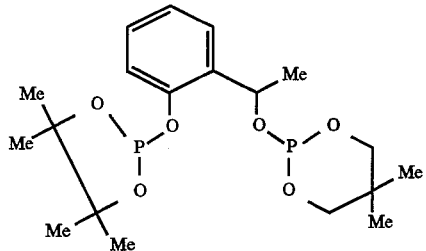

(66)

Now, a method for preparing the bisphosphite compound of the formula (I) of the present invention will be described. For example, the bisphosphite compound can readily be prepared by a method wherein (a) a phenol compound or an alcohol compound is reacted with phosphorus trichloride in a solvent such as toluene in the presence of a HCl receptor such as an amine to form the corresponding organic phosphoromonochloridite intermediates ClP(OR$^1$)(OR$^2$) and ClP (OR$^3$)(OR$^4$) wherein R$^1$ to R$^4$ are as defined in the formula (I), and (b) the intermediates are reacted with a hydroxyalkylphenol compound HO—W—L—OH, wherein W and L are as defined above with respect to the formula (I) in a solvent such as toluene in the presence of a HCl receptor such as an amine to form the corresponding bisphosphite compound.

The structural features of the novel nonsymmetric bisphosphite compound of the present invention are such that the crosslinked structure connecting the two phosphorus atoms is nonsymmetric, and that the environment around the phosphorus atom on one side is different from that around the other phosphorus atom. Therefore, the environments around the two types of phosphorus are different from each other sterically and electronically. Such environmental differences can be observed, for example, by the difference in the chemical shift in the $^{31}$P-NMR spectrum. When such two types of phosphorus atoms coordinate to the same Group VIII metal atom to form a chelate complex, the natures and behaviors of the coordinate bonds between the metal and the two phosphorus atoms are different from each other. Such differences reflect, for example, on a difference in the line widths of each peak assignable to two types of phosphorus atoms in the $^{31}$P-NMR spectrum when the bisphosphite compound of the present invention is co-existent with rhodium in a proper solvent.

The novel nonsymmetric bisphosphite compound of the present invention can be used as a ligand of a homogeneous metal catalyst for various organic reactions. It is particularly suitable for use as a constituting element of a complex catalyst which provides a high catalytic activity and selectivity for a straight chain isomer as aldehyde product in a hydroformylation reaction wherein an olefinic compound is reacted with carbon monoxide and hydrogen in the presence of a catalyst containing a phosphite compound and a Group VIII metal and whereby a side reaction due to reduction of the olefin scarcely takes place.

In the hydroformylation reaction, the bisphosphite compound of the formula (I) is useful as a constituting element of a complex catalyst which simultaneously satisfies (a) a high catalytic activity for the hydroformylation reaction, (b) high selectivity for a straight chain isomer as the resulting aldehyde and (c) suppression of the olefin reduction reaction. Among the above described phosphite compounds, the one wherein the distance between the two phosphorus atoms is too much, for example, the one wherein in the above formula (I) the X atom and the O atom are apart from each other by more than 11 covalent bonds through W and L, such a bisphosphite compound tends to hardly form chelate coordination on the rhodium atom, and accordingly is not suitable for use when it is desired to accomplish (b) the selectivity for an isomer of aldehyde and (c) suppression for the olefin reduction reaction at high levels. In a particularly preferred structure, W in the above formula (I) is an arylene group wherein two carbon atoms on the aromatic ring bonding to X and L are adjacent to each other. Further, in order to maintain (a) the catalytic activity for the hydroformylation reaction, (b) the selectivity for an isomer of aldehyde and (c) the suppression of the olefin reduction reaction, at high levels for a long period of time, it is preferred that each of R$^1$ to R$^4$ is a substituted or unsubstituted aryl group such as substituted or unsubstituted phenyl, naphthyl or anthracenyl, or a group of the structure wherein two aryl groups are crosslinked as represented by the above formula (III). A particularly preferred structure is a phenyl group having a hydrocarbon group at least at the o-position, a β-naphthyl group having a hydrocarbon group at least at the 3-position, or a structure wherein $R^1$ and $R^2$, or $R^3$ and $R^4$, are connected to each other at the respective o-positions by a covalent bond, as represented by the above formula (IV).

The novel bisphosphite of the present invention is structurally nonsymmetric, and the natures and behaviors of the two phosphorus atoms are different due to the nonsymmetry, whereby a metal complex coordinated by a phosphite compound is considered to provide a reactivity and selectivity which are different from those obtainable by conventional symmetric chelate ligand coordinating to a metal complex where the two phosphorus atoms are in the same environment, since a chemical species having one of the phosphorus atoms temporarily dissociated from the center atom, is likely to form.

The olefinic compound to be used as the starting material in the hydroformylation reaction of the present invention, is not particularly limited, so long as it is an organic compound having at least one olefinic double bond in its molecule. Specifically, it may, for example, be ethylene, propylene, butene, butadiene, pentene, heptene, hexadiene, octene, octadiene, nonene, decene, hexadecene, octadecene, eicosene, docosene, styrene, α-methylstyrene, cyclohexene, a lower olefin mixture such as a propylene/butene mixture, a n-butene/2-butene/isobutylene mixture or a n-butene/2-butene/isobutylene/butadiene mixture, an olefinic hydrocarbon such as a mixture of olefin oligomer isomers such as dimer to tetramer of a lower olefin such as propylene, n-butene or isobutylene, or a substituted olefin such as acrylonitrile, allyl alcohol, 1-hydroxy-2,7-octadiene, 3-hydroxy-1,7-octadiene, oleyl alcohol, 1-methoxy-2,7-octadiene, methyl acrylate, methyl methacrylate or methyl oleate. Among them, it is particularly preferred to employ an olefinic compound selected from the group consisting of propylene, butenes, butadiene, octenes, nonenes and mixtures thereof.

A compound as a source for supplying the Group VIII metal, may, for example, be a hydride, a halide, an organic salt, an inorganic salt, an oxide, a carbonyl compound, an amine compound, an olefine-coordinated compound, a phosphine-coordinated compound or a phosphite-coordinated compound of a Group VIII metal. For example, it may be a ruthenium compound such as ruthenium trichloride, tetraamminehydroxychlororuthenium chloride or dichlorotris(triphenylphosphine)ruthenium, a palladium compound such as palladium acetate or palladium chloride, an osmium compound such as osmium trichloride, an iridium compound such as iridium trichloride or iridium carbonyl, a platinum compound such as sodium hexachloroplatinate or potassium platinate, or cobalt compound such as dicobalt octacarbonyl or cobalt stearate, or a rhodium compound such as rhodium trichloride, rhodium nitrate, rhodium acetate, $Rh(acac)(CO)_2$, $[Rh(OAc)(COD)]_2$, $Rh_4(CO)_{12}$, $HRh(CO)(PPh_3)$, $[Rh(\mu-S(t-Bu))(CO)_2]_2$ wherein acac represents an acetylacetonate group, Ac an acetyl group, COD 1,5-cyclooctadiene, and t-Bu a t-butyl group. However, the Group VIII metal source is not limited to such specific examples.

The amount of the Group VIII metal is not particularly limited, and there is a limit from the viewpoint of the catalytic activity and the economical feasibility. It is usually selected so that the concentration in the hydroformylation reaction zone is within a range of from 0.05 mg to 5 g, preferably from 0.5 mg to 1 g, per 1 of the solvent for the reaction or the olefinic compound, as calculated as the metal.

The bisphosphite compound of the present invention may be used as preliminarily permitted to form a complex with the above Group VIII metal compound. The Group VIII metal complex containing the bisphosphite compound can readily be prepared by a conventional method for forming a complex from a Group VIII metal compound and the bisphosphite compound. In some cases, the Group VIII metal compound and the bisphosphite compound may be supplied to the hydroformylation reaction zone to form the complex there.

The amount of the bisphosphite compound of the present invention is not particularly limited, and it is selected usually within a range of from about 0.5 to 500 mols, preferably from 1 to 100 mols, per mol of the Group VIII metal.

Use of a solvent for the reaction is not essential for the hydroformylation reaction. However, a solvent inert to the hydroformylation reaction may be used as the case required. Specific examples of preferred solvents include aromatic hydrocarbon compounds such as toluene, xylene and dodecylbenzene, ketones such as acetone, diethyl ketone and methyl ethyl ketone, ethers such as tetrahydrofurane and dioxane, esters such as ethyl acetate and di-n-octyl-phthalate and high boiling components produced as by-products at the time of the hydroformylation reaction, such as condensation products of aldehyde.

The reaction conditions for the hydroformylation in the present invention may be the same as commonly employed theretofore. Namely, the reaction temperature is selected usually within a range of from 15° to 200° C., preferably from 50° to 150° C., and the reaction pressure is selected usually from atmospheric pressure to 200 atm, preferably from 5 to 100 atm, more preferably from 5 to 50 atm. The molar ratio of hydrogen to carbon monoxide ($H_2/CO$) is selected usually within a range of from 10/1 to 1/10, preferably from 1/1 to 6/1. The hydroformylation reaction system may be a continuous system or a batch system which may be conducted, for example, in an agitation type reactor or a bubbling column type reactor.

In a system where the novel bisphosphite compound of the present invention is employed, after separating the formed aldehyde by a method such as distillation, a recovered solution containing the Group VIII metal and the bisphosphite compound may be used to further conduct the hydroformylation reaction of an olefinic compound. Further, in a case where the olefinic compound is continuously converted to aldehyde, a part or whole of the resulting aldehyde is separated, and the residual liquid may be continuously recycled to the hydroformylation reactor.

Now, the present invention will be described in further detail with reference to Examples. However, it should be understood that the present invention is by no means restricted by such specific Examples.

EXAMPLE 1

Preparation of bisphosphite compounds (1) to (11)

A solution having 12.3 (48 mmol) of 3,6-di-t-butyl-2-naphthol and 5.83 g (58 mmol) of triethylamine dissolved in about 50 ml of toluene, was added dropwise to a toluene solution having 3.30 g (24 mmol) of $PCl_3$ dissolved in about 100 ml of toluene, at room temperature over a period of about 0.5 hour with stirring. After the dropwise addition, stirring was continued for about one hour. To the reaction solution containing phosphorochloridite intermediates thereby obtained, a solution having 1.5 g (12 mmol) of 2-hydroxymethyl phenol and 2.9 g (29 mmol) of triethylamine dissolved in about 50 ml of toluene, was then dropwise added at room temperature over a period of about 0.5 hour with stirring. After the dropwise addition, stirring was further continued for about 1 hour. Then, solid triethylamine hydrochloride formed as a by-product, was separated by filtration, and the filtrate was evaporated by vacuum distillation to obtain a residual solid. The solid was extracted with acetone and recrystallized to obtain bisphosphite (1) as colorless powdery solid.

Bisphosphite compounds (2), (5), (6) and (8) were prepared in the same manner as for bisphosphite compound (1) except that instead of 2-hydromethylphenol, 2-hydroxymethyl-5-t-butylphenol, 2-(1-hydroxyethyl)phenol, 2-(1-hydroxylethyl)-4,6-dimethylphenol and 3-hydroxymethyl-2-naphthol were used, respectively.

Further, bisphosphite compound (3) was prepared in the same manner as for bisphosphite compound (1) except that instead of 3,6-di-t-butyl-2-naphthol, 2,4-di-t-butylphenol was used, and instead of 2-hydroxymethyphenol, 2-hydroxymethyl-4,6-dimethylphenol was used. Furthermore, bisphosphite compounds (4), (7) and (9) were prepared in the same manner as for bisphosphite compound (1) except that instead of 3,6-di-t-butyl-2-naphthol, 2,4-di-t-butylphenol, 3,3'-di-t-butyl-5,5'-dimethoxy-2,2'-bisphenol and 2-isopropylphenol were used, respectively. Still further, bisphosphite compounds (10) and (11) were prepared in the same manner as for bisphosphite compound (5) except that instead of 3,6-di-t-butyl-2-naphthol, 2-isopropylphenol and 2-isopropyl-5-methylphenol were used, respectively.

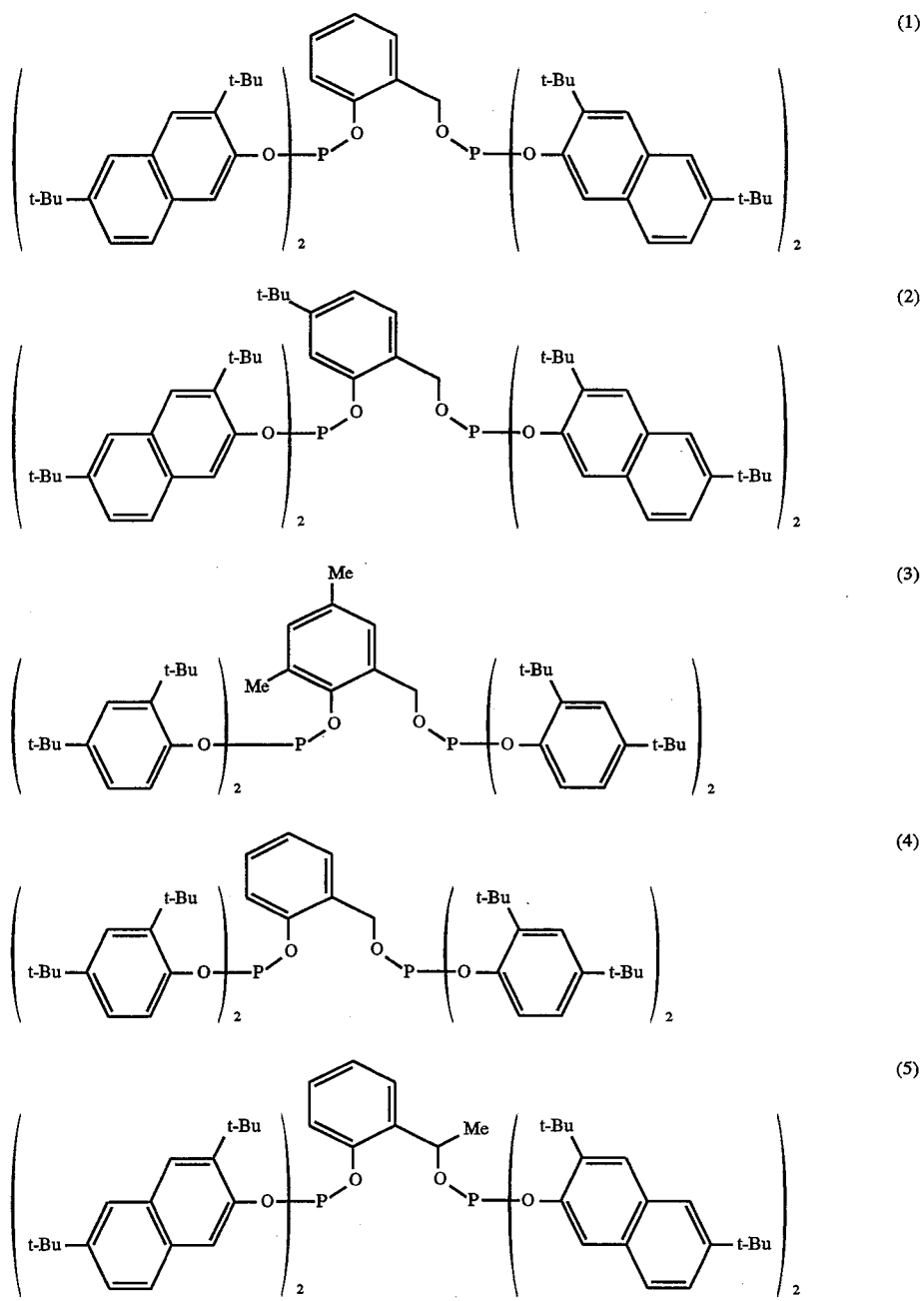

-continued
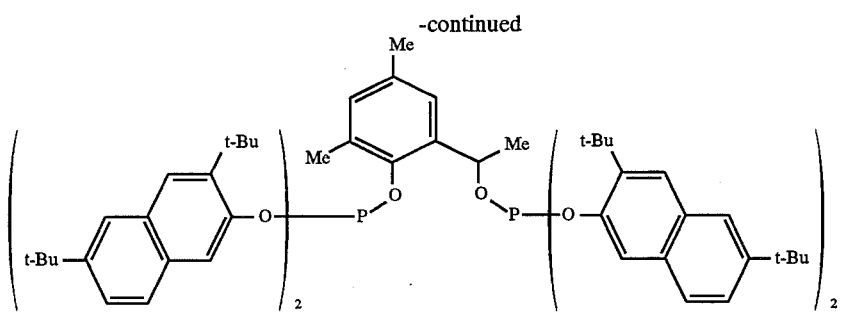
(6)
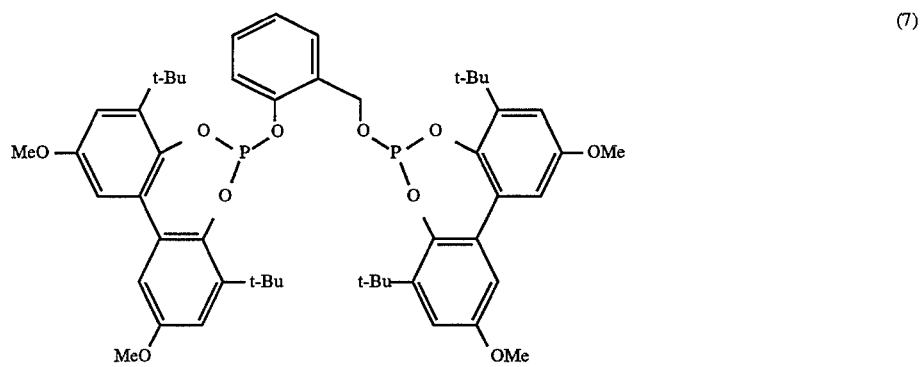
(7)
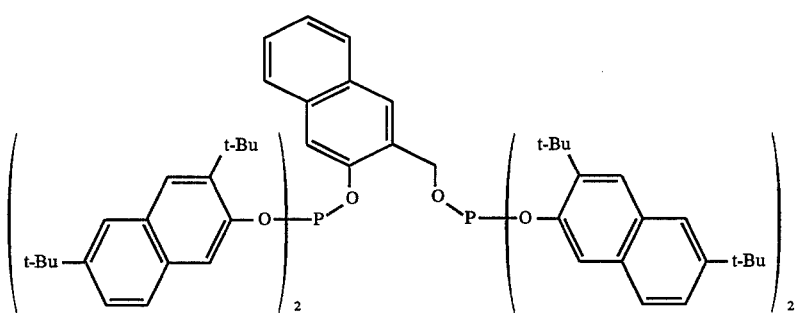
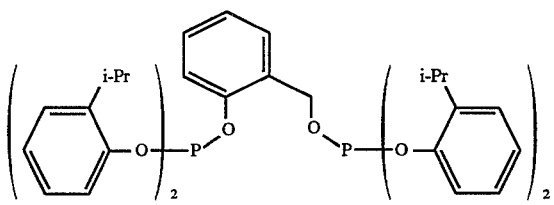
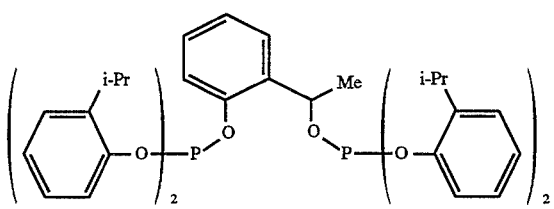
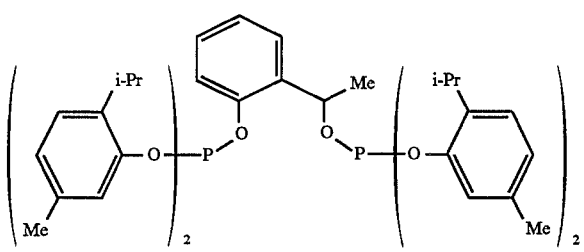
The structures of bisphosphite compounds (1) and (2) were confirmed by $^{31}$P-NMR (nuclear magnetic resonance spectrophotometry) (using Unity 300, manufactured by Valian Company), the elemental analysis and the mass spectrometry. Further, also with respect to bisphosphite compounds (3) to (11), it was confirmed by ¹H-NMR and ³¹P-NMR (using Unity 300, manufactured by Valian Company) that the desired compounds were obtained. The analytical values are shown in Table 1.

TABLE 1

| Ligand | | Elemental analysis (%) | | | Molecular weight[a] | ³¹P-NMR[c] (ppm) | |
|---|---|---|---|---|---|---|---|
| | | C | H | P | | | |
| (1) | Found | 78.72 | 8.21 | 5.08 | 1205 | 125.4 | 128.2 |
| | Calculated | 78.71 | 8.19 | 5.14 | 1205[b] | | |
| (2) | Found | 79.21 | 8.56 | 4.74 | 1261 | 125.1 | 127.9 |
| | Calculated | 79.01 | 8.47 | 4.91 | 1261[b] | | |
| (3) | | | | | | 127.5 | 136.7 |
| (4) | | | | | | 126.8 | 129.9 |
| (5) | | | | | | 128.7 | 128.9 |
| (6) | | | | | | 134.5 | 135.6 |
| (7) | | | | | | 135.4 | 135.9 |
| (8) | | | | | | 125.6 | 137.9 |
| (9) | | | | | | 129.8 | 130.7 |
| (10) | | | | | | 130.4 | 130.6 |
| (11) | | | | | | 130.56 | 130.57 |

[a] SIMS measurement.
[b] The calculated value of the molecular weight was calculated from the mass of the most stable isotope.
[c] Chemical shift based on phosphoric acid.

EXAMPLE 2

Into a top and bottom stirring type stainless steel autoclave having an internal capacity of 200 ml, 55 ml of toluene as a solvent, 5 ml of n-heptane as an internal standard, 40 mg of [Rh(OAc)(CO)]$_2$ and 4 mol per mol of the rhodium atom of asymmetric bisphosphite compound (1) (molar ratio of P/Rh=8) were charged under a nitrogen atmosphere, and then the autoclave was sealed. The interior of the autoclave was flushed three times with 10 kg/cm²G of nitrogen gas, and then the pressure was reduced to 0 kg/cm²G of nitrogen gas. Then, 4.5 g of propylene was injected thereto. The temperature was raised to 70° C., and synthesis gas (H$_2$/CO=1) was immediately injected so that the total pressure in the autoclave became 9 kg/cm²G inclusive of the pressure of propylene itself to initiate the reaction. The reaction was continued for three hours while synthesis gas consumed during the reaction was supplemented by a pressure accumulator via a secondary pressure controller to always maintain the total pressure in the reactor at a level of 9 kg/cm²G. After completion of the reaction, the reactor was cooled to room temperature, and the gas phase and the liquid phase in the autoclave were collected and subjected to the analyses of the respective components by means of gas chromatography. The yield of desired n-butyraldehyde was 87.4%, and yield of by-product propane was 0.6%.

EXAMPLE 3

The hydroformylation reaction of propylene was carried out in the same manner as in Example 2 except that instead of asymmetric bisphosphite compound (1), asymmetric bisphosphite compound (2) was used. The yield of desired n-butyraldehyde was 82.4% and the yield of by-product propane was 0.5%.

EXAMPLE 4

The hydroformylation reaction of propylene was carried out in the same manner as in Example 2 except that instead of asymmetric bisphosphite compound (1), asymmetric bisphosphite compound (3) was used, and the reaction time was changed to 5 hours. The yield of desired n-butyraldehyde was 81.6%, and the yield of by-product propane was 0.3%.

EXAMPLES 5 TO 9

The hydroformylation reaction of propylene was carried out in the same manner as in Example 2 except that reaction temperature, the reaction time and the ligand were changed as shown in Table 3, whereby the results as shown in Table 3 were obtained.

EXAMPLE 10

The hydroformylation reaction of propylene was carried out in the same manner as in Example 2 except that the reaction temperature was changed to 100° C., the total pressure in the autoclave was changed to 10 kg/cm²G, and the reaction time was changed to one hour By raising the reaction temperature, it was possible to obtain desired n-butyraldehyde in a short reaction time at a yield of as high as 87.2%. In spite of the high reaction temperature, the yield of by-product propane was as low as 1.1%.

EXAMPLE 11

The hydroformylation reaction of propylene was carried out in the same manner as in Example 10 except that instead of asymmetric bisphosphite compound (1), asymmetric bisphosphite compound (2) was used. The yield of desired n-butyraldehyde was 87.9%, and the yield of by-product propane was 1.1%.

EXAMPLE 12

The hydroformylation reaction of propylene was carried out in the same manner as in Example 10 except that instead of asymmetric bisphosphite compound (1), asymmetric bisphosphite compound (4) was used, and the reaction time was changed to 2 hours. The yield of desired n-butyraldehyde was 88.8%, and the yield of by-product propane was 1.5%.

EXAMPLE 13

The hydroformylation reaction of propylene was carried out in the same manner as in Example 10 except that instead of asymmetric bisphosphite compound (1), asymmetric bisphosphite compound (5) was used, and the reaction time was changed to 3 hours. The yield of desired n-butyraldehyde was 93.7%, and the yield of by-product propane was 0.9%.

Comparative Example 1

Preparation of symmetric bisphosphite compounds (A) and (B)

Symmetric bisphosphite (A) was prepared in the same manner for bisphosphite compound (1) except that instead of 2-hydroxymethylphenol, 1,3-propanediol was used. Further, symmetric bisphosphite (B) was prepared in the same manner for bisphosphite compound (1) except that 2,4-pentanediol was used.

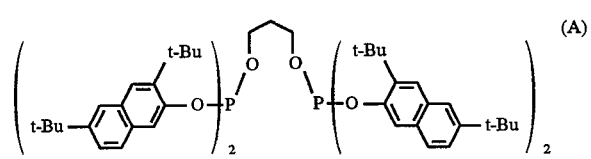

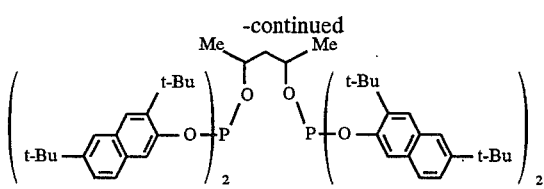

(B)

Comparative Example 2

The hydroformylation reaction of propylene was carried out in the same manner as in Example 2 except that instead of asymmetric bisphosphite compound (1), symmetric bisphosphite compound (A) was used. The yield of desired n-butyraldehyde was 86.8%, but the yield of by-product propane was as high as 2.3%.

Comparative Example 3

The hydroformylation reaction of propylene was carried out in the same manner as in Example 2 except that instead of asymmetric bisphosphite compound (1), symmetric bisphosphite compound (B) was used. The yield of desired n-butyraldehyde was 79.3%, and the yield of by-product propane was 1.7%.

Ccomparative Example 4

The hydroformylation reaction of propylene was carried out in the same manner as in Example 5 except that instead of asymmetric bisphosphite compound (1), symmetric bisphosphite compound (A) was used. The yield of desired n-butyraldehyde was 90.7%, but the yield of by-product propane was as high as 2.5%.

Comparative Example 5

The hydroformylation reaction of propylene was carried out in the same manner as in Example 5 except that instead of asymmetric bisphosphite compound (1), symmetric bisphosphite compound (B) was used. The yield of desired n-butyraldehyde was 82.4%, but the yield of by-product propane was as high as 3.5%.

The results of Examples 2 to 13 and Comparative Examples 2 to 5 are shown in Table 2.

TABLE 2

|  | Reaction temperature (°C.) | Reaction time (hr) | Ligand | Yield of n-butyraldehyde (%) | Yield of by-product propane (%) |
|---|---|---|---|---|---|
| Example 2 | 70 | 3 | Asymmetric (1) | 87.4 | 0.6 |
| Example 3 | 70 | 3 | Asymmetric (2) | 82.4 | 0.5 |
| Example 4 | 70 | 5 | Asymmetric (3) | 81.6 | 0.3 |
| Example 5 | 70 | 4 | Asymmetric (8) | 84.6 | 0.3 |
| [Example 5 | 70 | 3 | Asymmetric (8) | 78.6 | 0.2]* |
| Example 6 | 70 | 1.5 | Asymmetric (9) | 71.4 | 0.1 |
| Example 7 | 70 | 2 | Asymmetric (10) | 84.7 | 0.3 |
| Example 8 | 70 | 2 | Asymmetric (11) | 75.3 | 0.3 |
| Example 9 | 90 | 1.3 | Asymmetric (6) | 93.5 | 0.2 |
| Example 10 | 100 | 1 | Asymmetric (1) | 87.2 | 1.1 |
| Example 11 | 100 | 1 | Asymmetric (2) | 87.9 | 1.1 |
| Example 12 | 100 | 2 | Asymmetric (4) | 88.8 | 1.5 |
| Example 13 | 100 | 3 | Asymmetric (5) | 93.7 | 0.9 |
| Comparative Example 2 | 70 | 3 | Symmetric (A) | 86.8 | 2.3 |
| [Comparative Example 2 | 70 | 2 | Symmetric (A) | 41.7 | 1.1]* |
| [Comparative Example 2 | 70 | 1.5 | Symmetric (A) | 50.2 | 1.3]* |
| Comparative Example 3 | 70 | 3 | Symmetric (B) | 79.3 | 1.7 |
| Comparative Example 4 | 100 | 1 | Symmetric (A) | 90.7 | 2.5 |
| Comparative Example 5 | 100 | 1 | Symmetric (B) | 82.4 | 3.5 |

*The data at an intermediate point of the reaction, which are deduced based on the synthesis gas consumption monitored during the reactor.

From the results in Table 2, it is evident that when asymmetric bisphosphite compounds of the present invention are used (Examples), it is possible to control the yield of propane formed as a by-product by the reduction of the olefinic compound, as compared with the case where symmetric bisphosphite compounds are used (Comparative Examples).

The novel asymmetric bisphosphite compound of the present invention shows a high catalytic activity and high selectivity for a straight chain isomer as the aldehyde product in the hydroformylation reaction and is capable suppressing the side reaction i.e. the reduction of the olefinic compound, whereby the hydroformylation reaction can be carried out industrially advantageously.

What is claimed is:

1. A bisphosphite compound of the following formula (I):

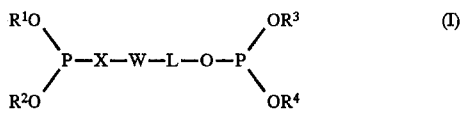

wherein W is a substituted or unsubstituted arylene group, L is a substituted or unsubstituted alkylene or alkenylene group, X is an oxygen atom, and each of $R^1$ to $R^4$ which are the same or different, is a substituted or unsubstituted alkyl, aryl, alkylaryl, arylalkyl or alicyclic group, or $R^1$ and $R^2$, and/or $R^3$ and $R^4$, bond to each other to form a ring.

2. The bisphosphite compound according to claim 1, wherein W in the formula (I) is an arylene group wherein two carbon atoms on an aromatic ring bonding to X and L are adjacent to each other.

3. The bisphosphite compound according to claim 1, wherein W in the formula (I) is a substituted or unsubstituted phenylene or naphthalene group.

4. The bisphosphite compound according to claim 3, wherein W in the formula (I) is a substituted or unsubstituted 1,2-phenylene group, 1,2-naphthylene group or 2,3-naphthylene group.

5. The bisphosphite compound according to claim 1, wherein L in the formula (I) is an alkylene group.

6. The bisphosphite compound according to claim 1, wherein each of $R^1$ to $R^4$ in the formula (I) is a substituted or unsubstituted aryl group.

7. The bisphosphite compound according to claim 6, wherein each of $R^1$ to $R^4$ in the formula (I) is a phenyl group having a hydrocarbon group at least at the o-position, or a β-naphthyl group having a hydrocarbon group at least at the 3-position.

8. The bisphosphite compound according to claim 1, wherein $R^1$ and $R^2$, and/or $R^3$ and $R^4$, in the formula (I), together form a group of the following formula (III):

wherein each of $Q^2$ and $Q^3$ is a substituted or unsubstituted arylene group, $R^6$ is a bivalent linking group, and p is an integer of 0 or 1.

9. The bisphosphite compound according to claim 8, wherein $R^1$ and $R^2$, and/or $R^3$ and $R^4$, in the formula (I), together form a group of the following formula (IV):

wherein $Q^5$ and $Q^6$ are substituted or unsubstituted arylene groups, which bond to each other at the respective o-positions via a covalent bond.

10. The bisphosphite compound according to claim 1, wherein $R^1$ and $R^2$, and/or $R^3$ and $R^4$, in the formula (I), together form a single arylene group which may have a substituent.

11. The bisphosphite compound according to claim 10, wherein $R^1$ and $R^2$, and/or $R^3$ and $R^4$, in the formula (I), together form a substituted or unsubstituted 1,2-phenylene group.

12. The bisphosphite compound according to claim 1, wherein in the formula (I), the X atom and the oxygen atom are apart from each other by from 4 to 10 covalent bonds through W and L.

* * * * *